(12) United States Patent
Wu et al.

(10) Patent No.: US 6,837,852 B2
(45) Date of Patent: Jan. 4, 2005

(54) CONTROL VALVE FOR SUCTION DEVICE FOR SURGICAL APPLICATIONS

(75) Inventors: Steven Zung-Hong Wu, Hillsborough, NJ (US); Christina Joy D'Arrigo, Morris Plains, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/185,393

(22) Filed: Jun. 28, 2002

(65) Prior Publication Data

US 2004/0002631 A1 Jan. 1, 2004

(51) Int. Cl.[7] .............................. A61B 1/32; A61M 1/00
(52) U.S. Cl. ........................................ 600/210; 604/35
(58) Field of Search ................................ 600/206, 210, 600/235; 604/35, 74, 75; 606/123

(56) References Cited

U.S. PATENT DOCUMENTS

| | | | | |
|---|---|---|---|---|
| 3,859,992 | A | * | 1/1975 | Amstutz ...................... 606/91 |
| 4,457,300 | A | | 7/1984 | Budde |
| 4,593,947 | A | * | 6/1986 | Yocum ....................... 294/64.1 |
| 5,865,730 | A | * | 2/1999 | Fox et al. .................... 600/228 |
| 5,890,516 | A | * | 4/1999 | Talamonti ................... 137/605 |
| 5,976,080 | A | | 11/1999 | Farascioni |
| 6,254,532 | B1 | | 7/2001 | Paolitto et al. |
| 6,306,085 | B1 | | 10/2001 | Farascioni |
| 6,331,157 | B2 | | 12/2001 | Hancock |
| 6,447,443 | B1 | * | 9/2002 | Keogh et al. ................. 600/37 |
| 6,506,149 | B2 | * | 1/2003 | Peng et al. ................... 600/37 |
| 6,517,563 | B1 | * | 2/2003 | Paolitto et al. ............. 606/205 |
| 6,558,314 | B1 | | 5/2003 | Adelman et al. |
| 6,641,604 | B1 | | 11/2003 | Adelman et al. |
| 2002/0091300 | A1 | | 7/2002 | Peng et al. |

FOREIGN PATENT DOCUMENTS

| | | | | |
|---|---|---|---|---|
| FR | 2774148 | * | 7/1999 | ........... F16M/11/06 |
| WO | WO 00/10468 | | 3/2000 | |

* cited by examiner

*Primary Examiner*—Eduardo C. Robert
*Assistant Examiner*—Anuradha Ramana

(57) ABSTRACT

A suction device for applying vacuum to a tissue surface is provided. The suction device including: a suction cup portion having a wall defining a cavity and an engagement surface for engaging the tissue surface; a vacuum inlet portion connected to the suction cup portion, the vacuum inlet portion having an inlet for connection to a vacuum source and a conduit in fluid communication with the vacuum inlet and the cavity such that a vacuum applied to the inlet is transferred to the cavity; and a valve disposed in the bore for selectively venting the vacuum in the cavity.

7 Claims, 10 Drawing Sheets

CONTROL VALVE FOR SUCTION DEVICE FOR SURGICAL APPLICATIONS

BACKGROUND OF THE INVENTION

1. Field of the Invention

The present invention relates generally to surgical devices, and more particularly, to a suction device for surgical applications in which an organ is supported by the suction device for improved access to the organ.

2. Prior Art

Surgical retractors are well known in the art. They are used in surgical procedures to maintain an opening in the skin to provide access to a body cavity and/or organ during surgery. Surgical retractors are often used in combination with accessories, such as suction devices for lifting, rotating, and/or supporting an organ. Such supporting is typically referred to as vacuum stabilization. Such suction devices and surgical retractors are particularly suited for cardiac bypass surgery.

While the suction devices of the prior art have their advantages, they are typically large in stature and accordingly obstruct a surgeon's view or access to the surgical field. The vacuum used to support the organ can be aggressive and cause tissue damage and tearing due to high vacuum settings (e.g., 400–700 mm HG). Typically, three-way valves are used for control of the vacuum. Therefore, the surgeon requires an assistant to operate (turn on and off) the valves. Furthermore, it becomes challenging to precisely control the vacuum by turning the valve on and off at a given time. Also, the suction cups of the suction devices are either inflexible or utilize an open-cell foam, both of which serve to cause trauma to the heart muscle and interfere with the heart's hemodynamic equilibrium. High vacuum pressure tends to push the attached tissue against the rim of the suction cup, which can cause damage to the heart tissue.

SUMMARY OF THE INVENTION

Therefore it is an object of the present invention to provide a suction device for surgical procedures that overcomes the problems associated with the prior art.

Accordingly, a suction device for applying vacuum to a tissue surface is provided. The suction device comprising: a suction cup portion having a wall defining a cavity and an engagement surface for engaging the tissue surface; a vacuum inlet portion connected to the suction cup portion, the vacuum inlet portion having an inlet for connection to a vacuum source and a conduit in fluid communication with the vacuum inlet and the cavity such that a vacuum applied to the inlet is transferred to the cavity; and a valve disposed in the bore for selectively venting the vacuum in the cavity.

Preferably, at least a portion of the conduit comprises an axial bore, the axial bore extending from the cavity to an outer surface of the vacuum inlet portion. Preferably, the suction device further comprises a vent hole in fluid communication with the axial bore and an ambient environment. Preferably, the valve comprises a seat for sealing engagement with a corresponding surface of the axial bore, the valve having vent means for selectively disengaging the seat against the corresponding surface to vent the cavity through the vent hole to the ambient environment.

The vent means preferably comprises a plunger slidingly disposed in the axial bore such that sliding of the plunger in an axial direction selectively disengages the seat from the corresponding surface of the axial bore. The suction device preferably further comprises a biasing means for biasing the plunger in an engaged position such that the seat is sealed against the corresponding surface. Preferably, the biasing means is a spring disposed in the axial bore circumferentially around the plunger.

The plunger preferably further has a button which extends beyond the outer surface, wherein depressing the button causes the plunger to slide in the axial direction. The vacuum inlet portion preferably further having a ball for adapting to a pivot joint, wherein the outer surface of the vacuum inlet portion corresponds to the ball.

Also provided is a surgical retractor comprising: means for retracting tissue surrounding an opening; at least one attachment member for mounting of accessories for use with the surgical retractor; and a suction device disposed on the attachment member for applying vacuum to a tissue surface, the suction device comprising: a suction cup portion having a wall defining a cavity and an engagement surface for engaging the tissue surface; a vacuum inlet portion connected to the suction cup portion, the vacuum inlet portion having an inlet for connection to a vacuum source and a conduit in fluid communication with the vacuum inlet and the cavity such that a vacuum applied to the inlet is transferred to the cavity; and a valve disposed in the bore for selectively venting the vacuum in the cavity.

Preferably, at least a portion of the conduit comprises an axial bore, the axial bore extending from the cavity to an outer surface of the vacuum inlet portion. Preferably, the suction device further comprises a vent hole in fluid communication with the axial bore and an ambient environment. Preferably, the valve comprises a seat for sealing engagement with a corresponding surface of the axial bore, the valve having vent means for selectively disengaging the seat against the corresponding surface to vent the cavity through the vent hole to the ambient environment.

The vent means preferably comprises a plunger slidingly disposed in the axial bore such that sliding of the plunger in an axial direction selectively disengages the seat from the corresponding surface of the axial bore. The suction device preferably further comprises a biasing means for biasing the plunger in an engaged position such that the seat is sealed against the corresponding surface. Preferably, the biasing means is a spring disposed in the axial bore circumferentially around the plunger.

The plunger preferably further has a button which extends beyond the outer surface, wherein depressing the button causes the plunger to slide in the axial direction. The vacuum inlet portion preferably further having a ball for adapting to a pivot joint, wherein the outer surface of the vacuum inlet portion corresponds to the ball.

BRIEF DESCRIPTION OF THE DRAWINGS

These and other features, aspects, and advantages of the apparatus and methods of the present invention will become better understood with regard to the following description, appended claims, and accompanying drawings where:

FIG. 3b illustrates a side view of the suction device and side rail of FIG. 3a.

DETAILED DESCRIPTION OF THE PREFERRED EMBODIMENT

Although this invention is applicable to numerous and various types of organs and surgical procedures, it has been found particularly useful in the environment of surgical procedures on the heart. Therefore, without limiting the applicability of the invention to surgical procedures on the heart, the invention will be described in such environment.

Figure 1:
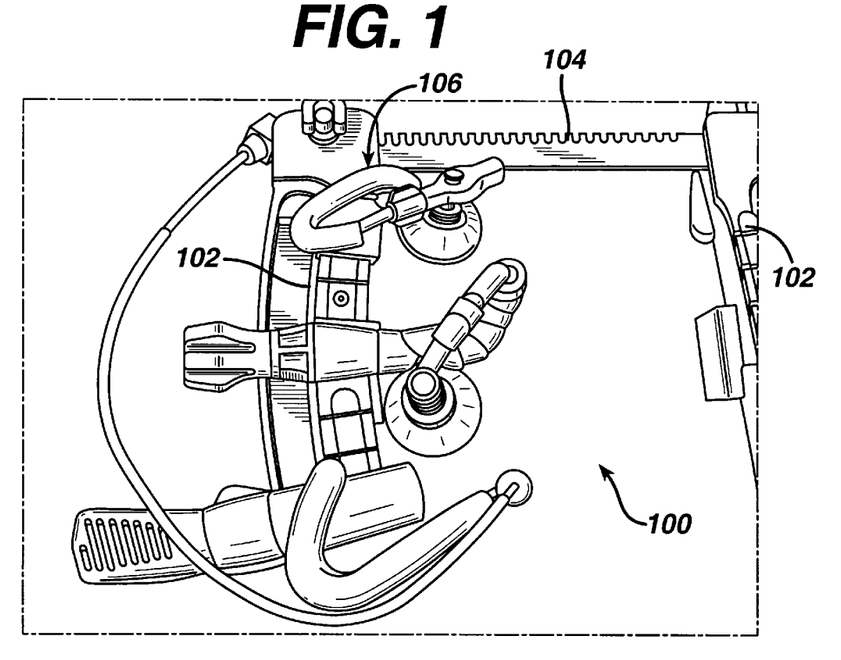
FIG. 1 illustrates a plan view of a surgical retractor device having a suction device mounted thereon.
Figure 2:
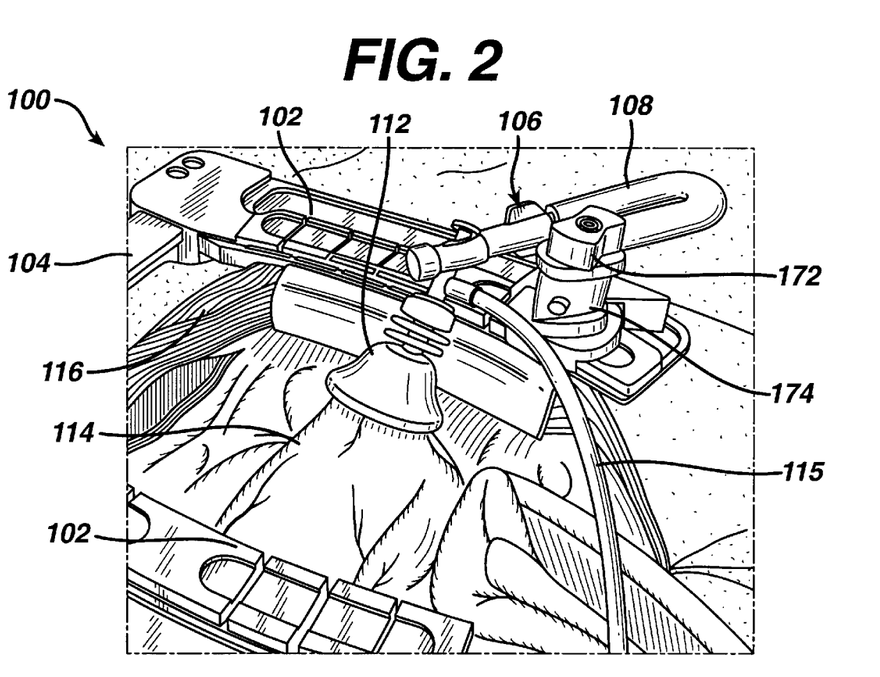
FIG. 2 illustrates a perspective view of the surgical retractor device of FIG. 1 shown in use for opening the chest wall to provide access to the heart, the suction device shown supporting the heart for improved access thereto.
Figure 3A:
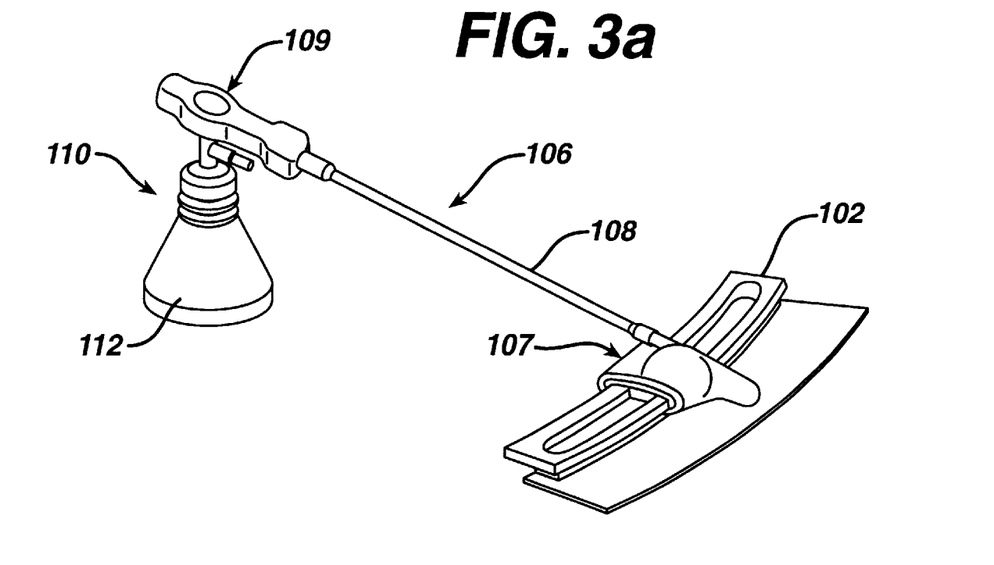
FIG. 3a illustrates an isometric view of a preferred implementation of a suction device for use with the surgical retractor device of FIG. 1, only the side rail of the surgical retractor being shown therein for clarity.

Referring now to FIGS. 1 and 2, there is illustrated a surgical retractor, generally referred to by reference numeral 100. The surgical retractor 100 is useful for retracting the skin to expose a body cavity and/or organ (alternatively referred to herein as "tissue") for performing a surgical procedure thereon. The surgical retractor generally has one or more attachment members for attachment of accessories, such as a suction device. The attachment members are preferably two side rails 102. The surgical retractor also has at least one transverse rail 104 upon which at least one of the side rails 102 is movable. One and preferably both side rails 102 have means, described fully below for holding accessories useful for the particular surgical procedure being performed. One such accessory is a suction device 106, which is useful for supporting an organ, such as the heart (shown in FIG. 3) during the surgical procedure to provide improved access to the organ and/or body cavity.

Figure 3B:
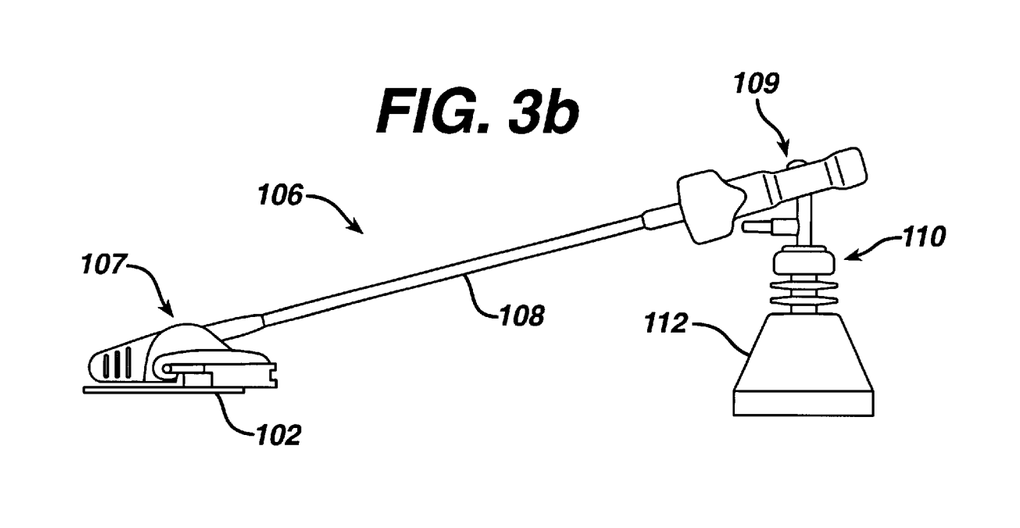

Referring now to FIGS. 3a and 3b, the suction device 106 typically has a means 107 for movably engaging the side rail, an arm 108, and a suction cup 110. The arm 108 is movable, preferably by being bendable, and typically cantilevers the suction cup 110 away from the side rail 102. The arm 108 is used to position the suction cup 110 over the organ, after which a suction cup portion 112 engages the organ with an applied vacuum to support the organ in a desired position. A ball joint 109 is provided to allow the suction cup portion 112 to rotate freely into any desired position. The arm 108 is further preferably rotatably disposed relative to the suction cup 110.

Referring back to FIG. 2, in a typical surgical procedure involving the heart 114, after the chest wall 116 is opened, the surgical retractor 100 is placed in the opening with the side rail(s) 102 engaging the opening. The side rails 102 are then slid on the transverse rail 104 to expand the size of the opening. The mounting means 107 is positioned on the side rail 102 and locked thereon to position the suction device 106 such that it will not be an obstruction to the surgical procedure. A vacuum is applied to the suction cup portion 112 by a vacuum source (not shown) and tubing 115. The arm 108 is positioned such that the suction cup portion 112 engages the heart 114 and applies the vacuum to a surface thereof, such as the apical region of the heart. The arm 108 is then raised to partially lift the heart 114 from the chest cavity and support it in the lifted position. In surgical retractors of the prior art, it is required for the arm 108 to be locked in position to support the heart 114. However, as will be discussed below, the suction device 106 of the present invention does not require the arm 108 to be locked.

Figure 4:
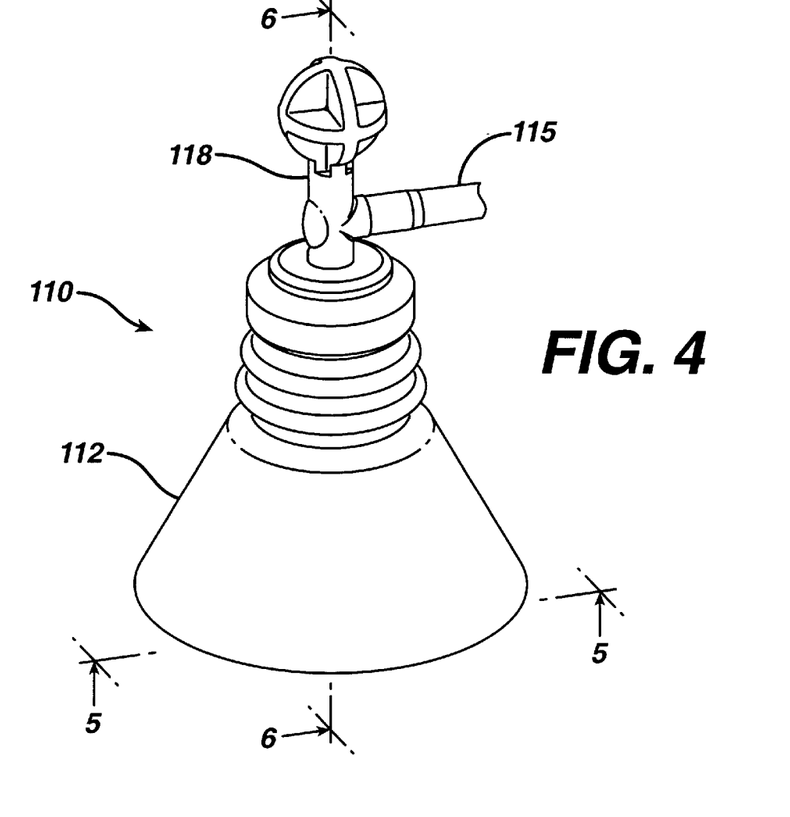
FIG. 4 illustrates a perspective view of a first preferred implementation of a suction cup of the present invention.
Figure 5:
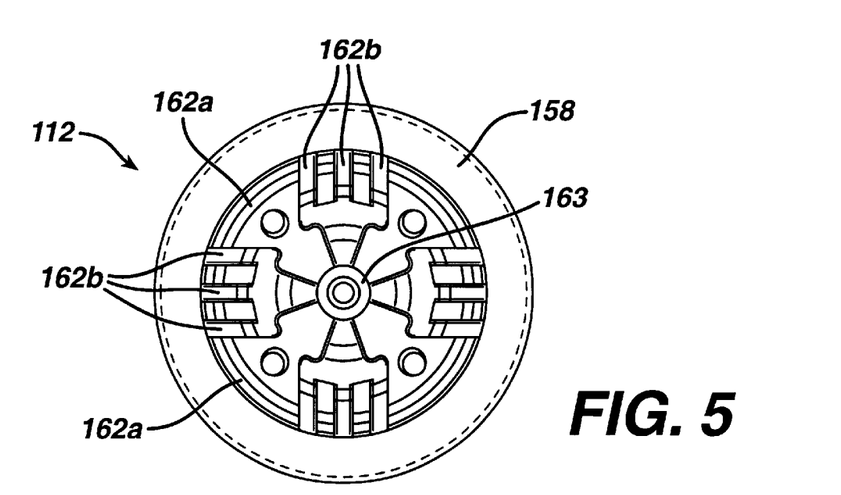
FIG. 5 illustrates a bottom view for the suction cup of FIG. 4 as seen from view 5—5.
Figure 6:
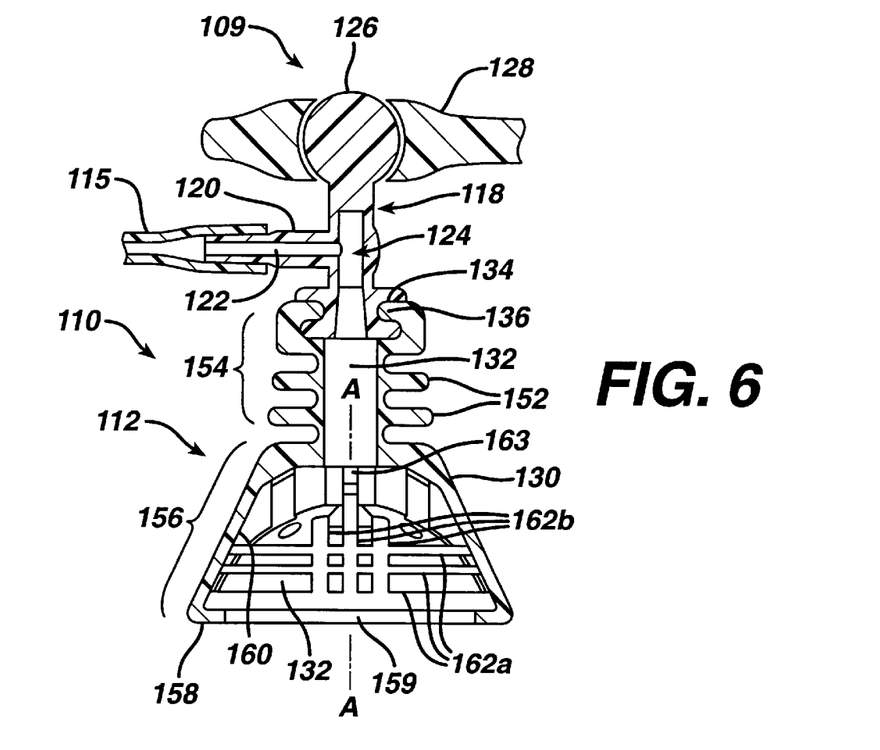
FIG. 6 illustrates a sectional view of the suction cup of FIG. 5 as taken along view 6—6 of FIG. 5.

Referring now to FIGS. 4–6, there is shown a preferred implementation of the suction cup 110 of the present invention. Although the suction cup 110 can be of single piece construction, it preferably comprises a suction cup portion 112 and a vacuum inlet portion 118. The suction cup portion 112 is preferably fabricated from a flexible material such as an elastomer. The elastomer is preferably polypropylene TPE (thermoplastic elastomer). The flexible suction cup portion material, such as c-flex, allows the heart to contract and torque, which allows the heart to maintain its hemodynamic equilibrium.

The vacuum inlet portion 118 is preferably a rigid or semi-rigid thermoplastic, such as polypropylene. The vacuum inlet portion 118 has a vacuum fitting 120, such as a hose barb, for connection to the vacuum tubing 115. The vacuum fitting 120 has a radial bore 122, which is in fluid communication with an axial bore 124. The vacuum inlet portion 118 further has a ball 126 at an end thereof. The ball 126 is rotatably disposed in a distal adapter 128 connected to a distal end of the arm 108 to form the pivot joint 109.

The suction cup portion 112 is disposed on the vacuum inlet portion 118. The suction cup portion 112 has a wall 130 which defines a cavity 132 which is in fluid communication with the axial bore 124. The vacuum inlet portion 118 and suction cup portion 112 can be fixed together in any manner known in the art. Preferably, the vacuum inlet portion 118 is provided with a channel 134 at an end thereof and the suction cup portion 112 is provided with a corresponding lip 136 which mates with and is fixedly retained in the channel 134.

Figure 7:
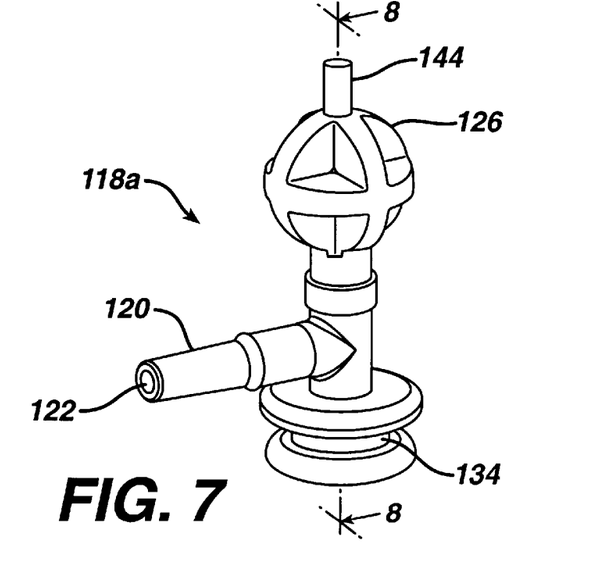
FIG. 7 illustrates an alternative version of a top portion of the suction cup of FIG. 4, the alternative version having a venting valve integrally formed therein.
Figure 8A:
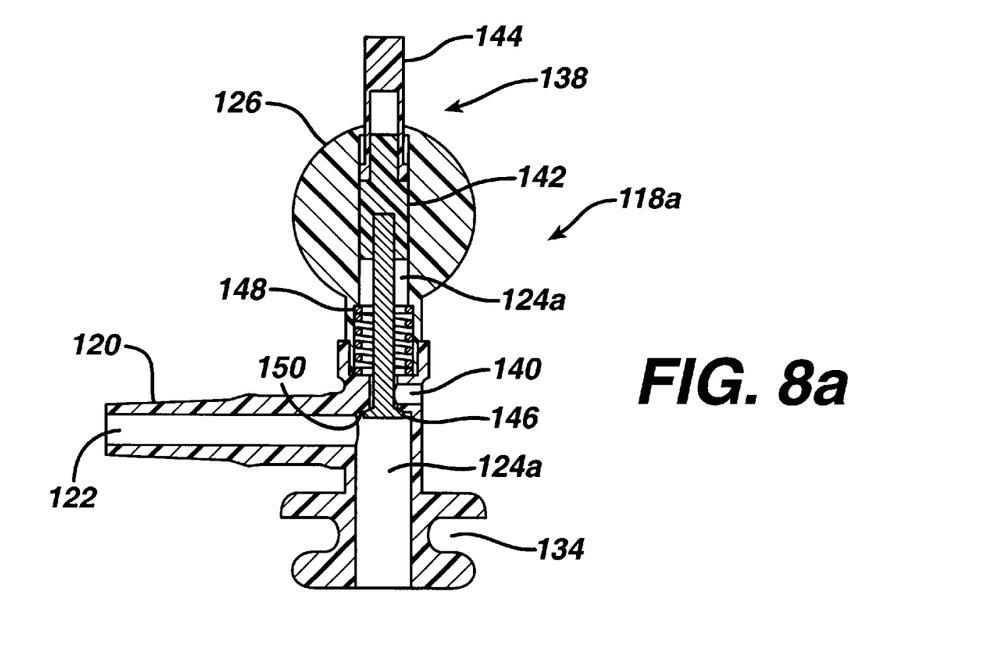
FIG. 8a illustrates a sectional view of the vacuum inlet portion of FIG. 7 as taken along line 8—8 of FIG. 7, the vacuum inlet portion being shown with the venting valve in the closed position.
Figure 8B:
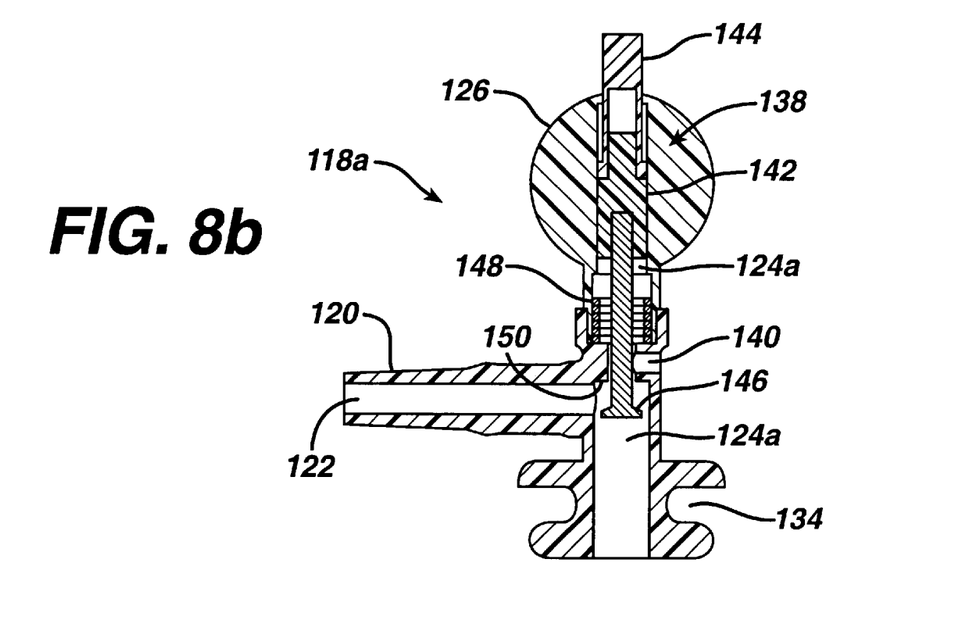
FIG. 8b illustrates a sectional view of the vacuum inlet portion of FIG. 7 as taken along line 8—8 of FIG. 7, the vacuum inlet portion being shown with the venting valve in the open (vented) position.

Referring now to FIGS. 7, 8a, and 8b, there is shown an alternative configuration of the vacuum inlet portion, referred to by reference numeral 118a and in which like numerals denote like features. Vacuum inlet portion 118a differs from vacuum inlet portion 118 in that it has an integral vacuum valve 138 disposed therein. In the alternatively configured vacuum inlet portion 118a illustrated in FIGS. 7, 8a, and 8b, the axial bore, referred to by reference numeral 124a extends throughout the axial length of the vacuum inlet portion 118a. The vacuum inlet portion 118a further has a vent hole 140 in fluid communication with the axial bore 124a. A plunger 142 is slidingly disposed in the axial bore 124a. The plunger 142 has a button 144 on one end thereof for actuating the valve 138 and a seat 146 on another end. A spring 148 is further disposed in the axial bore 124a for biasing the plunger 142 in a closed position illustrated in FIG. 8a in which the button 144 fully extends from the ball 126 and the seat 126 is seated and sealed against a corresponding surface 150 of the axial bore 124a. In the closed position, a vacuum applied to the radial bore 122 is in fluid communication with the cavity 132 of the suction cup portion 112 which can be applied to a surface of the tissue or organ to be supported. When the button 144 is depressed, the valve 138 is switched to an open position, as is illustrated in FIG. 8b. In the open position, the seat 146 is no longer seated against the corresponding surface 150 of the axial bore 124a and the vent hole 140 vents the vacuum applied to the axial bore 124a and cavity 132 to thereby turn the vacuum applied to the tissue or organ off.

Those skilled in the art will appreciate that the valve 138 allows a surgeon to control the applied vacuum independently with his thumb or fingertips and further allows the surgeon to place the suction cup portion 112 at the region where he/she desires and to turn the applied vacuum on or off at will without the need for an assistant. The vacuum valve 138 can be placed at the suction device itself with a button 144 control, as shown, or in another convenient area which permits the surgeon to easily operate the valve without the need for an assistant.

Referring back to FIGS. 5 and 6, there is shown a preferred implementation of the suction cup portion 112 of the suction cup 110. The wall 130 of the suction cup portion 112 preferably has a plurality of ribs 152 for adding flexibility to a neck portion 154 of the suction cup portion 112. The suction cup portion 112 further has a cupped portion 156 which flares outwardly from a central axis A from the neck portion 154 towards a lower rim 158. The lower rim 158 inverts towards the central axis A and defines an opening 159 into the cavity 132. The lower rim 158 further provides a sealing surface that engages against the organ/tissue.

An inner surface 160 of the cupped portion 156 preferably has a plurality of channels 162a, 162b formed thereon. The channels 162a, 162b are more preferably formed in both a circumferential and axial direction, the circumferential channels being referred to by reference numeral 162a and the axial channels being referred to by reference numeral 162b. Both the circumferential and axial channels 162a, 162b are formed at predetermined spacings along the inner surface 160 of the wall 130. Preferably, the axial channels 162 are interconnected at a common point, such as recessed portion 163. The circumferential and axial channels 162a, 162b allow the vacuum to be distributed evenly over the cupped cardiac region and also prevent the possibility of a vacuum line blockage.

Figure 9:
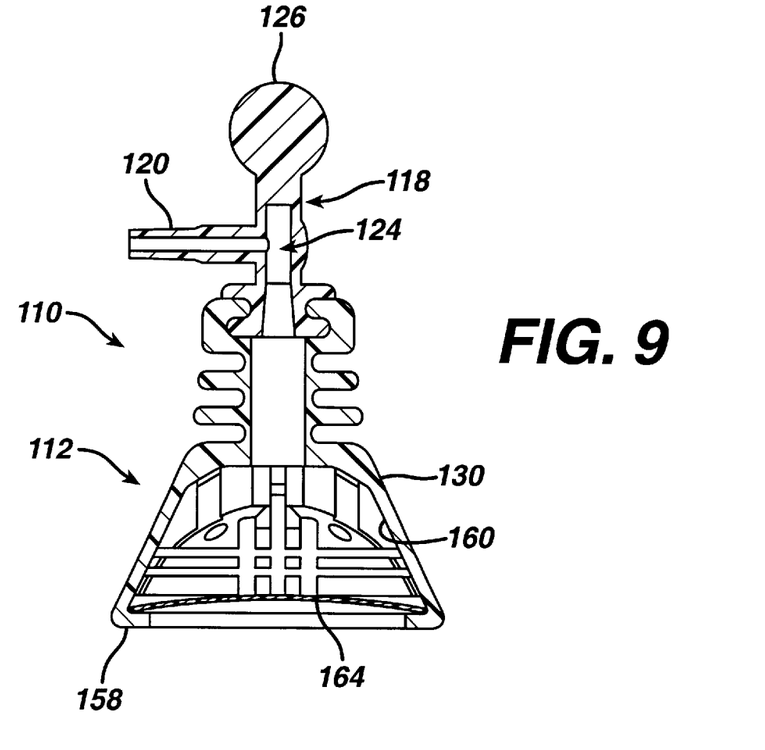
FIG. 9 illustrates an alternative version of the suction cup of FIG. 6, the alternative version having a mesh material inserted in the suction cup portion of the suction cup.

Referring now to FIG. 9, there is shown an alternative implementation of the suction cup portion 112 of the suction cup device 110 of the present invention. In the alternative implementation illustrated in FIG. 9, an elastic mesh 164 is disposed in the cavity 132 proximate the lower rim 158. The elastic mesh 164 material is preferably Merselene or Prolene or other elastic type material. Prolene and Merselene fiber mesh are non-absorbable knitted products that are flexible and compliant yet afford excellent strength, durability, and surgical adaptability. The elastic mesh 164 can be disposed on the suction cup or attached thereto, such as by bonding, heat staking, or by an o-ring support. If bonded, a bonding material such as lactite is preferably used to attach the elastic mesh 164 directly on the inner surface 160. If heat staked, the suction cup portion 112 material is melted onto a surface of the elastic mesh 164. Of course, in such a bond, the melting point for the suction cup portion 112 material is lower then the melting point for the elastic mesh 164 material. If supported with an o-ring (not shown), the o-ring of an elastic material is overmolded on the circumferential edge of the elastic mesh 164 and the mesh/o-ring combination is inserted into the cavity 132 without bonding, preferably at the junction between the wall 130 and the lower rim 158. The o-ring (not shown) retains the elastic mesh 164 in the cavity 132 and behind the lower rim 158 and also allows for added flexibility of the mesh.

Figure 10:
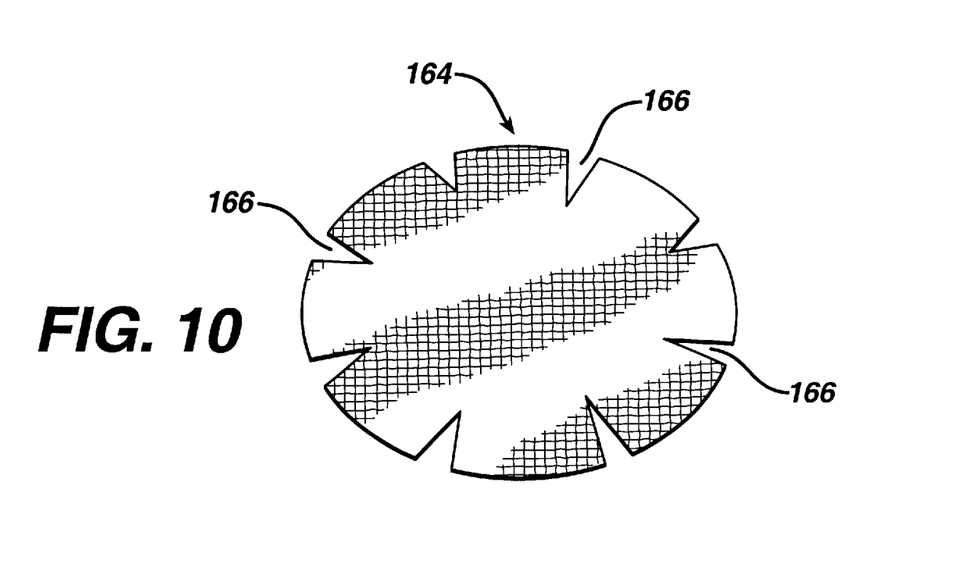
FIG. 10 illustrates a perspective view of the mesh material prior to insertion in the suction cup portion.

FIG. 10 illustrates the elastic mesh 164 prior to insertion in the cavity 132 of the suction cup portion 112. As shown in FIG. 9, the elastic mesh 164 is preferably inserted having a convex shape which engages the tissue or organ that is being supported. To facilitate the manipulation of the elastic mesh 164 into the convex shape, the elastic mesh 164 preferably has a plurality of triangular cut-outs 166 formed at equal spacings along its circumference. Those skilled in the art will appreciate that the elastic mesh 164 supports the tissue or organ as the suction retains the tissue or organ in position. The elastic mesh 164 also prevents tissue damage and minimizes the possibility of vacuum line clogging.

Figure 11:
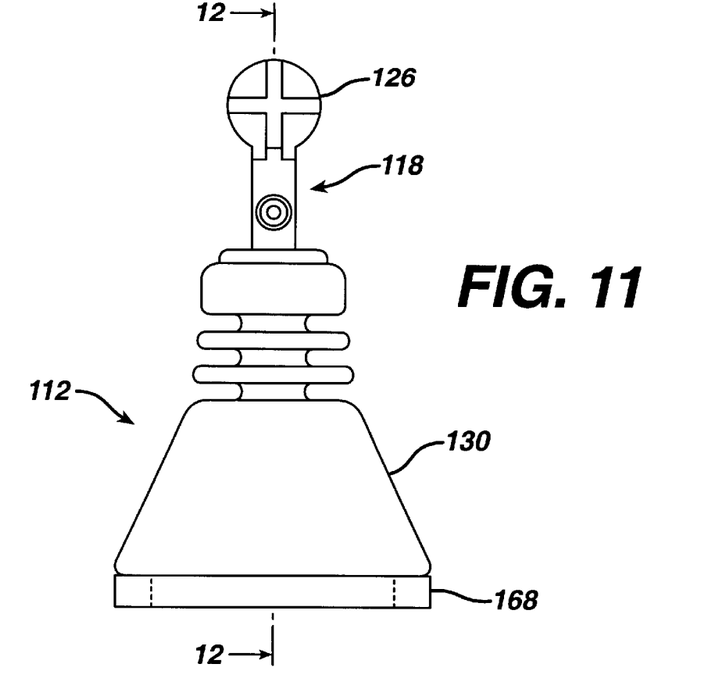
FIG. 11 illustrates a side view of yet another alternative version of the suction cup, the alternative version having a closed cell ring disposed on a lower rim of the suction cup portion of the suction cup.
Figure 12:
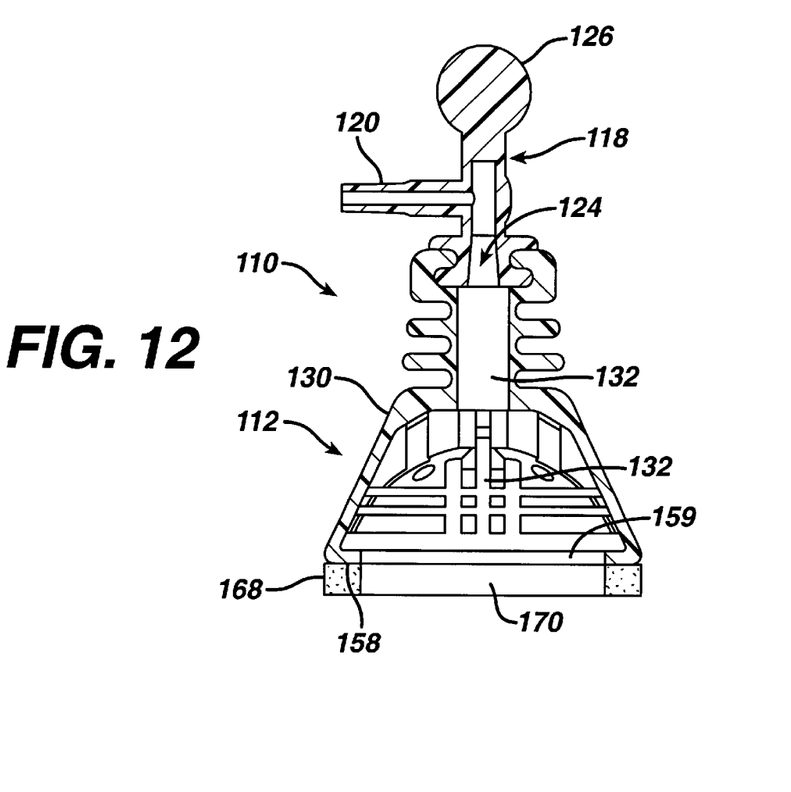
FIG. 12 illustrates a sectional view of the suction cup of FIG. 11 as taken along line 12—12 of FIG. 11.

Referring now to FIGS. 11 and 12, there is shown another alternative embodiment of the suction cup portion 112 of the suction cup 110 of the present invention. In the alternative version illustrated in FIGS. 11 and 12, a closed-cell foam 168 is disposed on the lower rim 158 to engage the organ or tissue to be supported. The closed cell foam 168 is preferably cylindrical and having an opening 170 corresponding with the opening 159 formed by the lower rim 158. The closed cell foam 168 is preferably a hydrophobic closed cell foam, such as polyethylene Ethyl vinyl acetate. The close cell foam 168 can be attached to the lower rim 158 by any means known in the art, such as by adhering with an epoxy, a solvent weld, or heat weld.

In a pig study, the hydrophobic close cell foam 168 on the lower rim 158 showed the best tissue/organ attachment compared to hydrophilic close cell foam, rubber, and silicone. In addition, the hydrophobic close cell foam 168 induced the least amount of tissue injury (ecchymosis) and conformed best to cardiac apical and lateral regions. The pig study also showed that the compliant characteristic of the close cell foam 168 was critical in conformability. Thus, the hydrophobic closed cell foam 168 on the lower rim 158 allows cardiac contraction while maintaining vacuum seal, secured attachment while minimizing tissue injury, and conforms to the apical and lateral attachment positions of the heart.

Although discussed separately, the circumferential and radial channels 162a, 162b, the elastic mesh 164, and the closed cell foam 168 can be used in any combination in the suction cup 112, including all such features.

Figure 13:
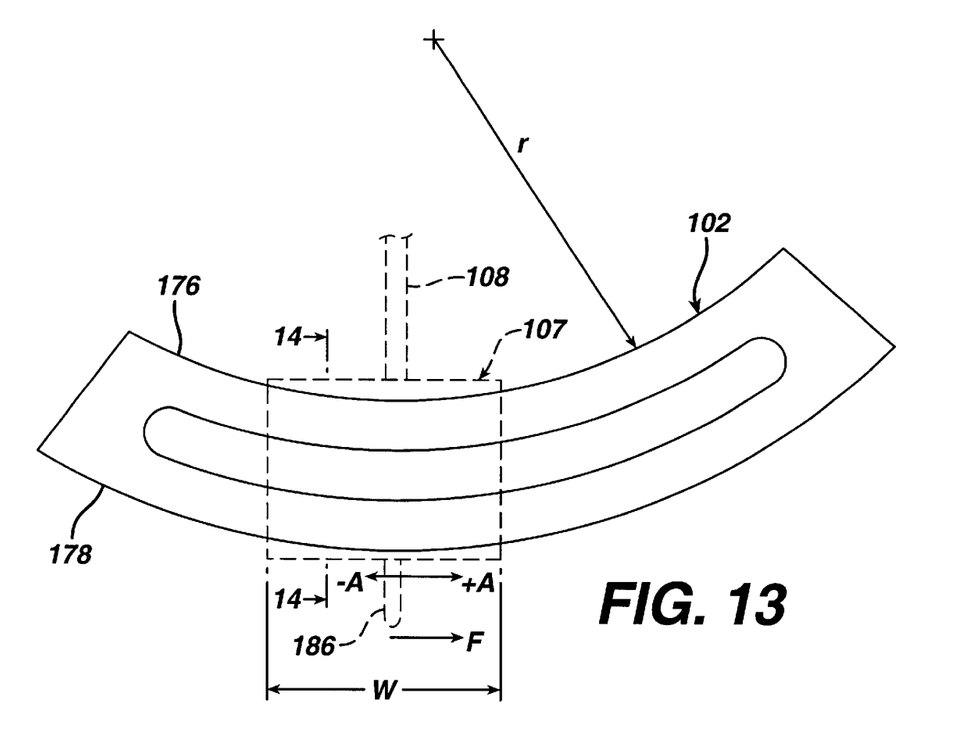
FIG. 13 illustrates a plan view of a side rail having a mounting means indicated in phantom lines.
Figure 14:
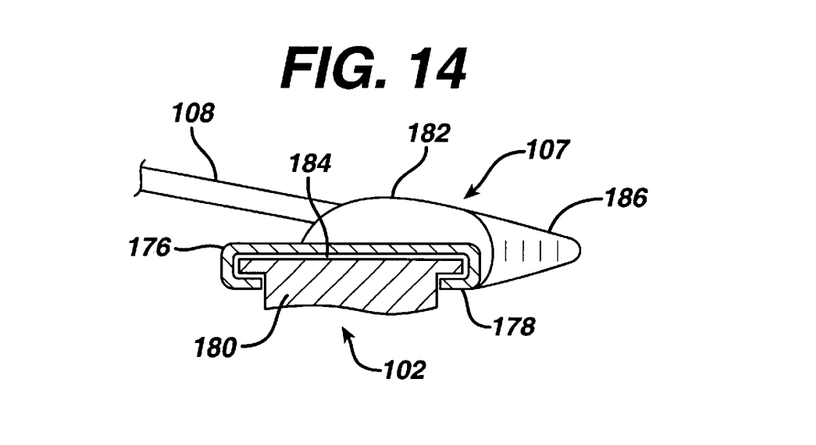
FIG. 14 illustrates a sectional view of the side rail and mounting means of FIG. 13 as taken along line 14—14 of FIG. 13.

Referring now to FIGS. 13 and 14, there is shown a preferred mounting means 107 for slidable attachment to the side rail 102. The mounting means 107 is shown in phantom lines in FIG. 13 to clearly show its relationship with the side rail 102. In addition to being slidable along the side rail 102 into a desired position, the mounting means 107 must also lock into the desired position to prevent further movement of the suction device 106 during the surgical procedure being performed. The suction device 106 can have any one of the typical mounting means known in the art, such as the screw down mount 107 shown in FIG. 2. The screw down mount 107 typically has a knob 172, a base 174, and a key (not shown). The knob 172 threadingly engages the key through the base 174 such that when the knob 172 is tightened, the key urges against a slot (not shown) on the underside of the side rail 102 to lock the suction device 106 in the desired position.

Referring back to FIGS. 13 and 14, a preferred mounting means 107 is shown. As illustrated in FIG. 13, the side rail 102 has at least one edge 176 (referred to hereinafter as a "first edge"), which is non-linear. Preferably, the side rail has a second edge 178 that mimics the curve of the first edge 176. The non-linearity of the first and second edges 176, 178 can be a simple radius (r) as is illustrated in FIG. 13, or it can be have a plurality of curved and/or straight segments. The first and second edges 176, 178 preferably are cantilevered from a base 180 of the side rail 102 to form a "t" cross-section. The mounting means 107 preferably has a body 182 having a channel 184 substantially corresponding to the "t" cross-section of the side rail 102. The channel 184 has a linear width (w) such that it can be wiggled (applying a back and forth motion along direction +/−A while maintaining a force (F) in the +A direction to move the body 182 in the +A direction) along the curved edges 176, 178 into a desired position and will stay locked in the desired position absent further wiggling of the body 182. To facilitate the wiggling of the body 182, a tab 186 is provided which protrudes from the body 182, preferably in a direction away from the opening in the body so as not to obstruct a surgeon's view or access into the body.

While the side rail 102 is shown by way of example as having non-linear edges 176, 178 and the body 182 of the mounting means 107 is shown having a linear channel 184 width, those skilled in the art will appreciate that an opposite configuration will function in the same manner. That is, a side rail 102 having straight edges (not shown) and a mounting means 107 having a body with a curved channel (not shown) will operate similarly to the configuration described above in that the mounting means 107 can be wiggled into a desired position and would remain in the desired position absent further wiggling. Furthermore, while the side rail 102 is described by way of example as having cantilevered edges 176, 178, and the body 182 of the mounting means 107 is described as having a corresponding channel 184, those skilled in the art will also appreciate that the body 182 of the mounting means 107 can have cantilevered edges (not shown) and the side rail 102 can have a corresponding channel (not shown). Such an alterative configuration would also have the same intended function as the configurations described above in that the body 182 can be wiggled into a desired position and remain there absent further wiggling. Those skilled in the art will appreciate that the preferred mounting means 107, in any of the configurations discussed above, provides several advantages over the screw down type of mounting means of the prior art. For example, the mounting means 107 described above is less complicated and more economical since it has no moving parts. Furthermore, the preferred mounting means 107 described above requires a single hand for manipulation thereof, thus, eliminating the need for an assistant for placement and locking of the suction device 106 into a desired position.

Referring now to FIGS. 15a, 15b, 16a, 16b, 17a, and 17b, there are shown cross-sectional views of three variations of a mounting means 107. Each of the mounting means 107 has a body 182 having a channel 184 formed therein. The channel 184 may have a straight or curved width and may be utilized with the preferred mounting means as discussed above with regard to FIGS. 13 and 14, or the channel 184 may be used with other mounting means known in the art, such as a screw down type. Each of the channels 184 depicted in the mounting means 107 of FIGS. 15a, 15b, 16a, 16b, 17a, and 17b, engage a side rail 102 having a base 180 with cantilevered edges 176, 178.

Figure 15A:
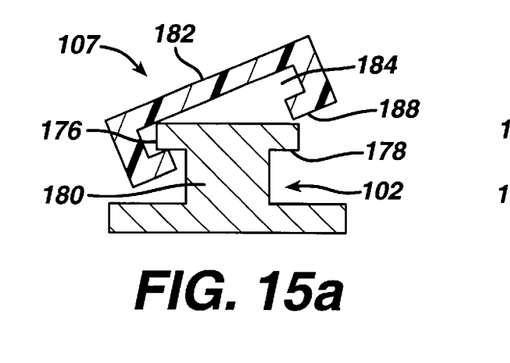
FIGS. 15a and 15b illustrate sectional views of an alternative version of a mounting means, FIG. 15a showing the mounting means before being secured to the side rail and FIG. 15b showing the mounting means after being secured to the side rail.
Figure 15B:
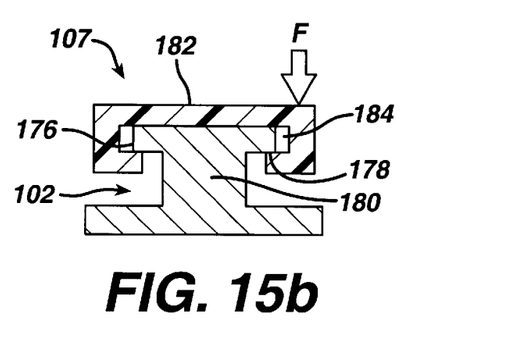

Referring specifically to FIGS. 15a and 15b, a first variation of the mounting means 107 is shown in which a force F is required in the direction of arrow F to secure the mounting means 107 on the side rail 102. FIG. 15a shows a slight interference between a portion 188 of the body 182 of the mounting means 107 and one of the edges (shown as the second edge 178) of the base 180 of the side rail 102. Such interference exists when the other of the edges (shown as the first edge 176) is placed in a corresponding portion of the channel 184 and the interference portion 188 rests on the other edge 178. A downward force F is applied to the body 182 in the vicinity of the interference portion 188 to force the second edge 178 into a corresponding portion of the channel 184 as shown in FIG. 15b. This type of fit between mating parts is commonly referred to as a "snap" fit. To facilitate the snap fit between the body 182 of the mounting means 107 and the base 180 of the side rail 102, at least a portion of the body 182 is preferably fabricated from a material having enough elasticity to plastically deform under the applied force F. Preferably, at least the body 182 of the mounting means 107 corresponding to the channel 184 is made from a thermoplastic, such as polypropylene.

Figure 16A:
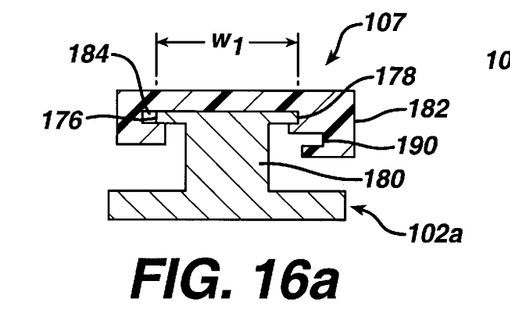
FIGS. 16a and 16b illustrate sectional views of an alternative version of a mounting means secured to side rails of varying width.
Figure 16B:
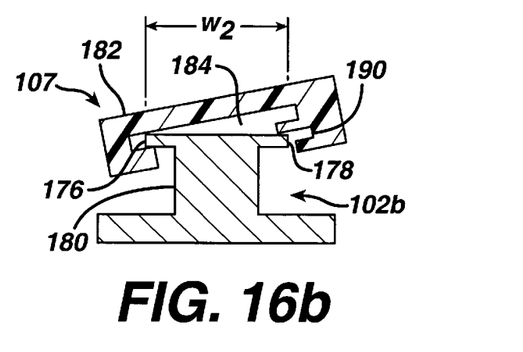

Referring now specifically to FIGS. 16a and 16b, there is shown a second variation of the mounting means 107. In the second variation, the body 182 of the mounting means 107 has a channel 184 with at least one extra slotted portion 190 for accommodating side rails 102 of varying widths w1, w2. FIG. 16a shows a side rail 102a having a first width w1 between the first and second edges 176, 178. The body 182 of the mounting means 107 is shown secured on the base 180 of the side rail 102a such that the first and second edges 176, 178 are disposed in the channel 184 and the mounting means 107 is substantially coplanar with the side rail 102a. FIG. 16b shows a side rail 102b having a second width w2, greater than the first width w1. However, the same mounting means 107 can accommodate either of the side rails 102a, 102b. As shown in FIG. 16b, one of the edges (shown as the first edge 176) is disposed in a corresponding portion of the channel 184 as discussed above. However, the other of the edges (shown as the second edge 178) is disposed in the extra slotted portion 190. Although in this configuration, the body 182 of the mounting means 107 is slightly inclined with respect to the side rail 102b, the operation of the suction device 106 is not altered due to the articulation of the arm 108 and the pivoting of the suction cup 110 relative to the arm 108 provided by the pivot 109.

Figure 17A:
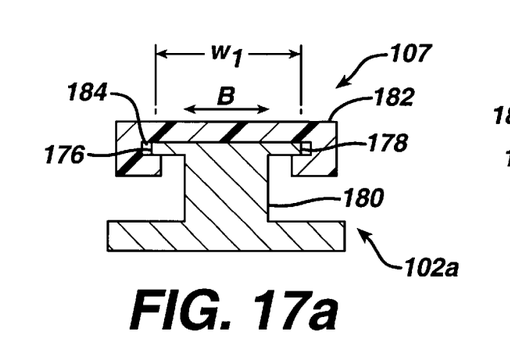
FIGS. 17a and 17b illustrate sectional views of yet another alternative version of a mounting means, FIGS. 17a and 17b showing the mounting means secured to side rails of varying width.
Figure 17B:
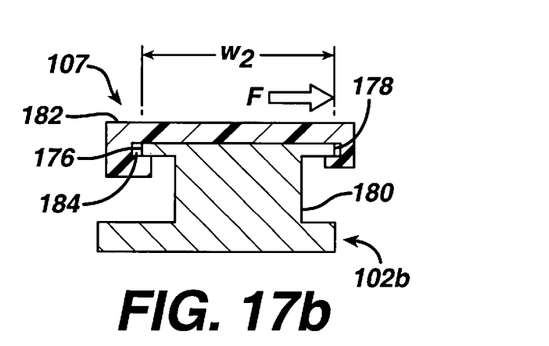

Referring now specifically to FIGS. 17a and 17b, there is shown a third version of the mounting means 107, which like the second version shown in FIGS. 16a and 16b, can accommodate side rails 102 of different widths w1, w2. FIG. 17a shows the body 182 of the mounting means 107 secured on the side rail 102a. Specifically, the first and second edges 176, 178 are disposed in corresponding portions of the channel 184. The body 182 of the mounting means, or at least the portion of the body 182 corresponding to the channel 184 is fabricated from a stretchable material, such as an elastomer, such that it can be stretched in the direction of arrow B. A preferred elastomer is polypropylene. FIG. 17a shows the body 182 in a relaxed (unstretched) state secured on a side rail 102a having a width w1 between the first and second edges 176, 178. FIG. 17b shows the same body 182 stretched in direction B by the application of a force F to fit over a side rail 102b having a width w2, greater than width w1. Those skilled in the art will appreciate that unlike the second version shown in FIGS. 16a and 16b, the third version of the mounting means 107 can accommodate side rails 102 having a range of widths.

Figure 18:
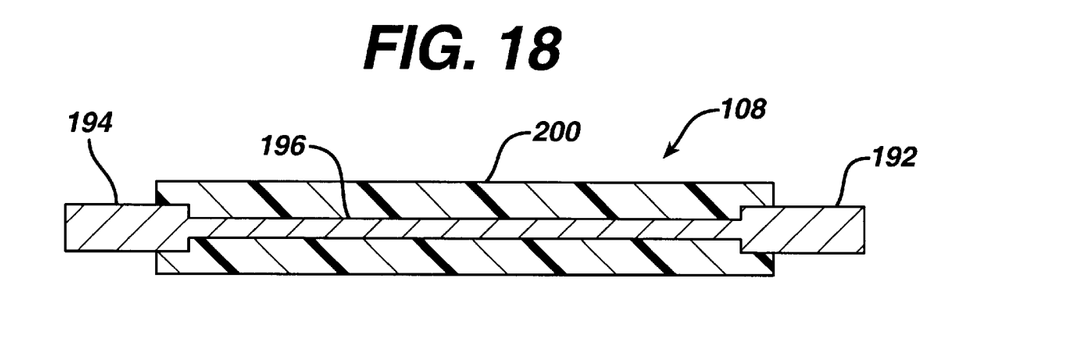
FIGS. 18 and 19 illustrate sectional views of first and second variations of an arm for use with the suction devices of the present invention.
Figure 19:
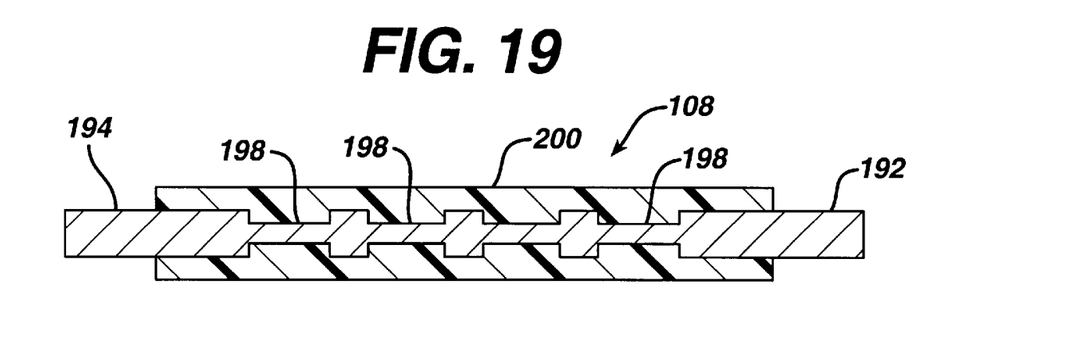

Referring now to FIGS. 18 and 19, there is illustrated the arm 108 of the suction device 106. The arm 108 is shown in FIGS. 18 and 19 apart from its mating portions of the suction device 106. A first end of the arm 192 is fixed in the mounting means, preferably, by a force fit, braze, or other means known in the art. A second end 194 of the arm 194 is disposed in the distal adaptor 128, preferably in a rotating fashion. The arm 108 is preferably of a unitary construction having a central undercut portion 196, or alternatively, a series of undercut portions 198 as shown in FIG. 19. The arm 108 is fabricated from a malleable material which can be deformed into a desired shape yet still be resilient enough to remain in such deformed position to support an organ or tissue cantilevered at the suction cup 110. Preferably, the malleable material is a type 304 annealed stainless steel.

The arm 108 can be used in either a straight configuration, as shown in FIGS. 3a and 3b, or in a curved configuration, as shown in FIGS. 1 and 2. A cushion material 200 is preferably disposed around all portions of the arm 108 except the first and second ends 192, 194. The cushion material 200 can be prefabricated and applied on the arm 108 or molded directly onto the arm 108. The cushion material can be any flexible material, such as c-flex, which aids in the resiliency of the arm. Those skilled in the art will appreciate that the arm 108 of the present invention has many advantages over the arms of the prior art, including, simplicity of design (contains no moving parts), ease of operation (does not have to be actuated into and out of a locked position), and low profile (does not encumber the surgeons view or access to the surgical site.

While there has been shown and described what are considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A suction device for applying vacuum to a tissue surface, the suction device comprising:
   a suction cup portion having a wall defining a cavity and an engagement surface for engaging the tissue surface;
   a vacuum inlet portion connected to the suction cup portion, the vacuum inlet portion having an inlet for connection to a vacuum source and a conduit in fluid communication with the vacuum inlet and the cavity such that a vacuum applied to the inlet is transferred to the cavity, at least a portion of the conduit comprising an axial bore extending from the cavity to an outer surface of the vacuum inlet portion;
   a valve disposed in the vacuum inlet for selectively venting the vacuum in the cavity, the valve comprising a seat for sealing engagement with a corresponding surface of the axial bore; and
   a vent hole in fluid communication with the conduit and an ambient environment;
   wherein the valve has vent means for selectively disengaging the seat against the corresponding surface of the axial bore to vent the cavity through the vent hole to the ambient environment, the vent means comprising a plunger slidingly disposed in the axial bore such that sliding of the plunger in an axial direction selectively disengages the seat from the corresponding surface of the axial bore.

2. The suction device of claim 1, further comprising a biasing means for biasing the plunger in an engaged position such that the seat is sealed against the corresponding surface of the axial bore.

3. The suction device of claim 2, wherein the biasing means is a spring disposed in the axial bore circumferentially around the plunger.

4. The suction device of claim 1, wherein the plunger further has a button which extends beyond the outer surface, wherein depressing the button causes the plunger to slide in the axial direction.

5. The suction device of claim 4, wherein the vacuum inlet portion further has a ball for adapting to a pivot joint, wherein the outer surface of the vacuum inlet portion corresponds to the ball.

6. The suction device according to claim 1, wherein the suction device is disposed on an attachment member mounted to a surgical retractor.

7. The suction device according to claim 6, wherein the surgical retractor comprises means for retracting tissue surrounding an opening.

* * * * *